(12) United States Patent
Zhao et al.

(10) Patent No.: US 10,585,050 B2
(45) Date of Patent: Mar. 10, 2020

(54) METHODS AND DEVICES FOR DETECTING RADIOACTIVE SOURCES

(71) Applicant: Nuctech Company Limited, Beijing (CN)

(72) Inventors: Kun Zhao, Beijing (CN); Qiang Wang, Beijing (CN); Yangtian Zhang, Beijing (CN); Hua Peng, Beijing (CN); Yuanjing Li, Beijing (CN)

(73) Assignee: Nuctech Company Limited, Beijing (CN)

(*) Notice: Subject to any disclaimer, the term of this patent is extended or adjusted under 35 U.S.C. 154(b) by 0 days.

(21) Appl. No.: 15/720,639

(22) Filed: Sep. 29, 2017

(65) Prior Publication Data

US 2018/0024078 A1 Jan. 25, 2018

Related U.S. Application Data

(63) Continuation of application No. PCT/CN2016/086138, filed on Jun. 17, 2016.

(30) Foreign Application Priority Data

Sep. 9, 2015 (CN) .......................... 2015 1 0569821

(51) Int. Cl.
| | | |
|---|---|---|
| *G01T 1/167* | (2006.01) | |
| *G01N 23/00* | (2006.01) | |
| *G01V 5/00* | (2006.01) | |

(52) U.S. Cl.
CPC ............. *G01N 23/00* (2013.01); *G01T 1/167* (2013.01); *G01V 5/0075* (2013.01)

(58) Field of Classification Search
CPC ....... G01N 23/00; G01T 1/167; G01V 5/0075
See application file for complete search history.

(56) References Cited

U.S. PATENT DOCUMENTS

| | | | | | |
|---|---|---|---|---|---|
| 3,794,843 | A | * | 2/1974 | Chen ...................... | G01N 23/09 250/359.1 |
| 4,582,992 | A | * | 4/1986 | Atwell ................... | G01N 23/12 250/357.1 |

(Continued)

FOREIGN PATENT DOCUMENTS

| | | |
|---|---|---|
| CN | 1598553 A | 3/2005 |
| CN | 103424766 A | 12/2013 |

(Continued)

OTHER PUBLICATIONS

International Search Report with Translation for International Application No. PCT/CN2016/086138 dated Sep. 20, 2016.

(Continued)

*Primary Examiner* — David P Porta
*Assistant Examiner* — Djura Malevic
(74) *Attorney, Agent, or Firm* — Knobbe, Martens, Olson & Bear, LLP

(57) ABSTRACT

A method and device for detecting radioactive sources is disclosed. In one aspect, an example method includes measuring, by a detector, a count rate curve of an inspection object while the inspection object moves through the detector. Pattern recognition is performed on the count rate curve. Whether there are radioactive sources in the inspection object is determined according to a result of the pattern recognition, and if there are radioactive sources in the inspection object, a type of the radioactive sources is determined.

14 Claims, 5 Drawing Sheets

(56) References Cited

U.S. PATENT DOCUMENTS

| | | | |
|---|---|---|---|
| 4,864,129 A * | 9/1989 | Paske | G01V 5/12 250/269.3 |
| 6,462,343 B1 | 10/2002 | Choo | |
| 6,768,421 B1 * | 7/2004 | Alioto | B66C 19/002 340/600 |
| 7,550,738 B1 * | 6/2009 | DeVito | G01T 1/167 250/393 |
| 7,709,800 B2 | 5/2010 | Proctor et al. | |
| 7,813,540 B1 * | 10/2010 | Kraft | G01V 5/0016 378/57 |
| 8,119,993 B2 | 2/2012 | van Bree et al. | |
| 8,487,240 B2 * | 7/2013 | Koehl | G01N 27/66 250/281 |
| 8,536,515 B2 * | 9/2013 | Masse | G01T 1/169 250/252.1 |
| 8,886,497 B1 * | 11/2014 | Vold | G06F 17/13 703/2 |
| 9,488,602 B2 | 11/2016 | Kobayashi et al. | |
| 9,864,091 B2 | 1/2018 | Chen et al. | |
| 2003/0043380 A1 * | 3/2003 | Deck | G02B 27/48 356/450 |
| 2003/0178560 A1 * | 9/2003 | Odom | G01V 5/104 250/269.2 |
| 2004/0195517 A1 * | 10/2004 | Rowland | G01T 1/244 250/370.15 |
| 2005/0023477 A1 * | 2/2005 | Archer | G01T 7/00 250/370.11 |
| 2006/0157655 A1 | 7/2006 | Mammone et al. | |
| 2006/0193421 A1 * | 8/2006 | Orr | G01N 23/10 376/156 |
| 2006/0284094 A1 * | 12/2006 | Inbar | G01V 5/0075 250/359.1 |
| 2007/0295911 A1 * | 12/2007 | Sved | G01T 3/00 250/359.1 |
| 2008/0023631 A1 * | 1/2008 | Majors | G01V 5/0075 250/336.1 |
| 2008/0157986 A1 | 7/2008 | Proctor et al. | |
| 2008/0191887 A1 * | 8/2008 | Mullikin | G01T 1/167 340/600 |
| 2010/0305873 A1 * | 12/2010 | Sjoden | G01T 1/362 702/30 |
| 2010/0312532 A1 * | 12/2010 | Masse | G01T 1/169 703/2 |
| 2010/0324871 A1 * | 12/2010 | Masse | G08B 21/12 703/2 |
| 2011/0056371 A1 * | 3/2011 | Koehl | G01N 27/66 95/78 |
| 2011/0266454 A1 | 11/2011 | van Bree et al. | |
| 2012/0155702 A1 * | 6/2012 | Kraft | G01V 5/0016 382/103 |
| 2013/0229510 A1 * | 9/2013 | Killmann | B07C 5/3416 348/91 |
| 2014/0299784 A1 | 10/2014 | Kobayashi et al. | |
| 2014/0314200 A1 | 10/2014 | Chen et al. | |
| 2014/0320640 A1 * | 10/2014 | Barbier | G01B 11/26 348/135 |
| 2017/0167865 A1 * | 6/2017 | Welle | G01B 21/20 |

FOREIGN PATENT DOCUMENTS

| | | | | |
|---|---|---|---|---|
| CN | 103674979 A | | 3/2014 | |
| CN | 104040374 A | | 9/2014 | |
| CN | 104459755 A | | 3/2015 | |
| CN | 104570035 A | | 4/2015 | |
| GB | 2236851 A | * | 4/1991 | G01V 5/12 |

OTHER PUBLICATIONS

Office Action dated Jul. 2, 2018 in Chinese Patent Application No. 201510569821.1 and English translation thereof, which corresponds in priority to the above-identified U.S. application.

Robinson et al., "Time Series Evaluation of Radiation Portal Monitor Data for Point Source Detection," IEEE Transaction on Nuclear Science, vol. 56, No. 6, Dec. 2009.

Office Action Issued for Canadian Application No. 2,981,201 dated May 7, 2019, which corresponds in priority to above-identified subject U.S. Application.

Extended European Search Report for Application No. 16843501.4 dated Apr. 17, 2019, which corresponds in priority to above-identified subject U.S. Application.

* cited by examiner

METHODS AND DEVICES FOR DETECTING RADIOACTIVE SOURCES

RELATED APPLICATIONS

Any and all priority claims identified in the Application Data Sheet, or any correction thereto, are hereby incorporated by reference under 37 CFR 1.57. This application claims priority to, and is a continuation of, International Application No. PCT/CN2016/086138, filed on Jun. 17, 2016. This application further claims priority to Chinese Application No. 201510569821.1, filed on Sep. 9, 2015. Each application is hereby incorporated by reference in its entirety for all purposes.

TECHNICAL FIELD

The disclosed technology relates to the field of radioactive source detection, and more particularly, to a method and device for detecting radioactive sources.

BACKGROUND

Devices for detecting radioactive sources (for example, portal monitors for detecting moving radioactive sources) are devices for prevention of smuggling and illegally carrying radioactive material, and they are playing an increasingly important role in fields such as customs, inspection and quarantine, etc. With the popularity and mass use of such devices, higher requirements are taken into consideration for these devices. For example, an urgent problem for such devices is that there are often innocent alarms triggered by naturally occurring radioactive material (such as chemical fertilizers, bananas, ceramics, marble, etc.) during the use of the devices, and these alarms account for a considerable proportion in all the alarm events. In the absence of any action, this would add a lot of work to the staff (especially in ports with a high throughput), and thus greatly reduces the efficiency of custom clearance.

In order to reduce the negative impact of these alarms on operations in the ports, there is proposed a solution of determining the types of radioactive sources (innocent or not) by manually observing the shape of a count rate profile. The solution has been applied to large-scale ports with a lot of devices, and has improved the efficiency of clearance to a certain extent.

However, although the method of manually observing can solve the above problem to a certain extent, in order to implement this solution, in-depth and meticulous training for picture observing staff are required, and the observing staff will have to concentrate all the time during work, which is an unnecessary burden. Taking China Custom as an example, custom officers need to work in a job rotation mechanism, which means that a new round of training will be required after each round of rotation, and the experience that accumulated by the last group of picture observing staff will result in nothing. In addition, the picture observing staff typically have to work for a long shift, which may cause them difficult to maintain concentration throughout the entire shift time. Job positions may be increased so that the work shift for a single person will be reduced, however, this will not ensure a better observing level, and on the other hand, will increases the personnel burden for the administration of the custom.

SUMMARY

In order to solve at least one of the above problems in the conventional method, the disclosed technology proposes a method and device for detecting radioactive sources.

According to an aspect of the disclosed technology, there is proposed a method for detecting radioactive sources, comprising: measuring, by a detector, a count rate curve of an inspection object while the inspection object moves through the detector; performing pattern recognition on the count rate curve; and determining whether there are radioactive sources in the inspection object according to a result of the pattern recognition and determining a type of the radioactive sources if there are radioactive sources in the inspection object.

In one embodiment, the method further comprises: determining whether movement of the inspection object satisfies a predetermined condition, and if the movement of the inspection object does not satisfy the predetermined condition, causing the inspection object to move through the detector again and accordingly performing the measurement, pattern recognition and determination operations.

In one embodiment, the predetermined condition is that the inspection object did not stop during the movement or a minimum moving speed of the movement was higher than a threshold speed.

In one embodiment, the operation of performing pattern recognition on the count rate curve comprises: calculating mathematical characteristics of the count rate curve; and performing pattern recognition according to a result of the calculation.

In one embodiment, the operation of performing the pattern recognition comprises performing pattern matching with a plurality of predetermined patterns.

In one embodiment, the mathematical characteristics are a kurtosis of the curve or magnitude of decrease on both sides of a maximum value of the curve.

In one embodiment, the count rate curve is a count rate curve from which a background mean value has been removed.

In one embodiment, the method further comprises: performing pattern recognition on the count rate curve only if a maximum count rate value in the count rate curve of the inspection object is higher than an alarm threshold.

According to another aspect of the disclosed technology, there is further proposed a device for detecting radioactive sources, comprising: a detector configured to detect an inspection object passing therethrough (e.g., moves through the detector); a processor connected to the detector and configured to perform operations of: obtaining a count rate curve of the inspection object according to an inspection result from the detector; performing pattern recognition on the count rate curve; and determining whether there are radioactive sources in the inspection object according to a result of the pattern recognition and determining a type of the radioactive sources if there are radioactive sources in the inspection object.

In one embodiment, the processor is further configured to perform operations of: determining whether movement of the inspection object satisfies a predetermined condition, and if the movement of the inspection object does not satisfy the predetermined condition, causing the inspection object to move through the detector again and accordingly performing the detection, pattern recognition and determination operations.

In one embodiment, the predetermined condition is that the inspection object did not stop during the movement or a minimum moving speed of the movement was higher than a threshold speed.

In one embodiment, the operation of performing pattern recognition on the count rate curve comprises: calculating mathematical characteristics of the count rate curve; and performing pattern recognition according to a result of the calculation.

In one embodiment, performing the pattern recognition comprises performing pattern matching with a plurality of predetermined patterns.

In one embodiment, the mathematical characteristics are a kurtosis of the curve or magnitude of decrease on both sides of a maximum value of the curve.

In one embodiment, the count rate curve is a count rate curve from which a background mean value has been removed.

In one embodiment, the processor is further configured to: perform pattern recognition on the count rate curve only if a maximum count rate value in the count rate curve of the inspection object is higher than an alarm threshold.

The disclosed technology proposes a device and method for detecting radioactive sources according to a pattern for count rate changes during detection, so as to be able to effectively determine a type of the radioactive sources (point sources or bulk sources), thereby reducing a number of false alarms triggered by naturally occurring radioactive material and improving the operation efficiency. This technology is suitable for places where a portal device for detecting radioactive material in a vehicle is installed, such as custom ports, etc.

DETAILED DESCRIPTION

The disclosed technology will be described in detail below with reference to the accompanying drawings.

Firstly, a typical process of detecting moving radioactive material using a portal device will be described with reference to FIGS. 1-4.

Figure 1:
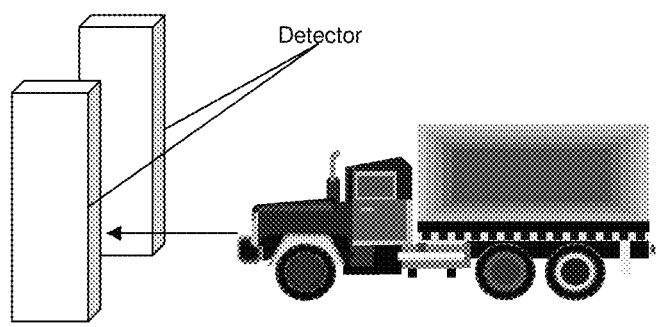
FIG. 1 is a diagram of a typical portal device for detecting moving radioactive sources.

FIG. 1 is a diagram of a typical portal device for detecting moving radioactive sources. The detection device comprises a detector (e.g., two detection pillars standing on both sides of a passage, respectively), and an inspection object passes through the passage between the two pillars to achieve detection of the radioactive material. The inspection object may be moved in a variety of ways. For example, the detection device may be a device for inspecting a vehicle, and thereby the inspection object passes through the detection device in a vehicle-mounted manner. For example, the inspection object is preferably a container. FIG. 1 is illustrated by taking a vehicle-mounted inspection object as an example. It will be understood by those skilled in the art that in different use scenarios, the inspection object may also be caused to pass through the passage between the two detection pillars in other manners, for example, using a conveyer band, a slide, a ship, etc.

A count rate is a number of pulses received by the detector per unit time due to radiation from radioactive material. The count rate reflects intensity of the radiation.

Figure 2:
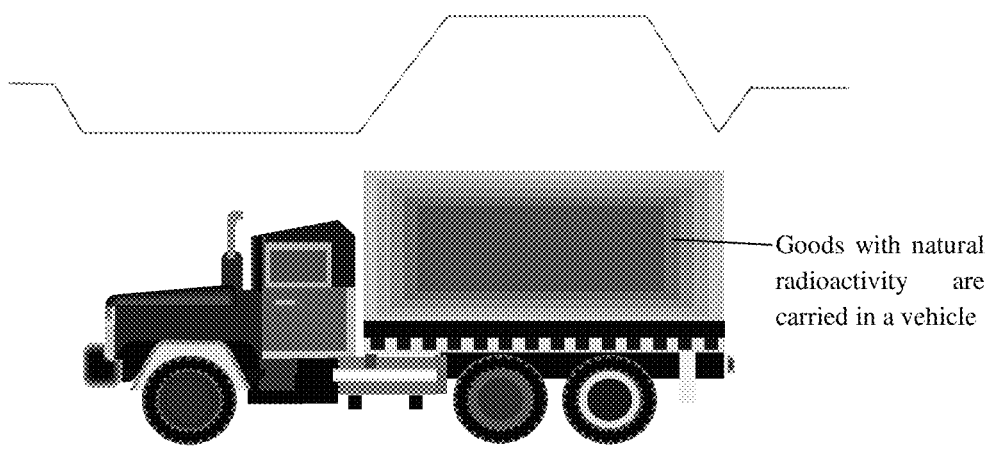
FIG. 2 illustrates a diagram of a shape of a count rate curve of naturally occurring radioactive material in a detection process.
Figure 3:
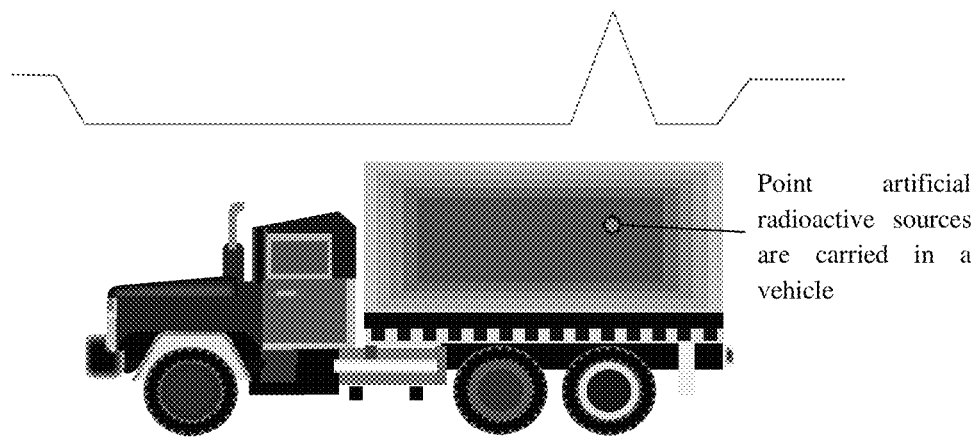
FIG. 3 illustrates a diagram of a shape of a count rate curve of artificial radioactive sources (point radioactive sources) in a detection process.

FIG. 2 illustrates a diagram of a shape of a count rate curve of naturally occurring radioactive material in a detection process. FIG. 3 illustrates a diagram of a shape of a count rate curve of artificial radioactive sources (point radioactive sources) in a detection process. In general, the count rate curve satisfies one or more of the following:

before a head of a vehicle enters the passage, the curve reflects a background level;

after the head of the vehicle enters the passage, the count rate decreases as the detector is blocked by the head of the vehicle;

if a separation between the head of the vehicle and a body of the vehicle is large to form a large gap, the count rate increases when the gap passes through a front surface of the detector (and the count rate does not increase if there is no significant separation between the head of the vehicle and the body of the vehicle);

when the body of the vehicle enters the passage, the count rate decreases again (if it has increased before), and magnitude of the decrease is determined by a type and an amount of goods loaded on the vehicle, which is usually between 10% and 30%, and has a gentle fluctuation; and after the vehicle leaves the passage, the count rate restores to the background level.

In addition, it can be seen from comparison between FIG. 2 and FIG. 3 that a difference between the shapes of the count rate curves produced by the point radioactive sources and the bulk radioactive sources is very obvious, wherein the count rate curve of the point radioactive sources is in a spike shape, and the count rate curve of the bulk radioactive sources is much more gentle (a degree of gentleness depends on uniformity of a distribution of the bulk radioactive sources).

Figure 4:
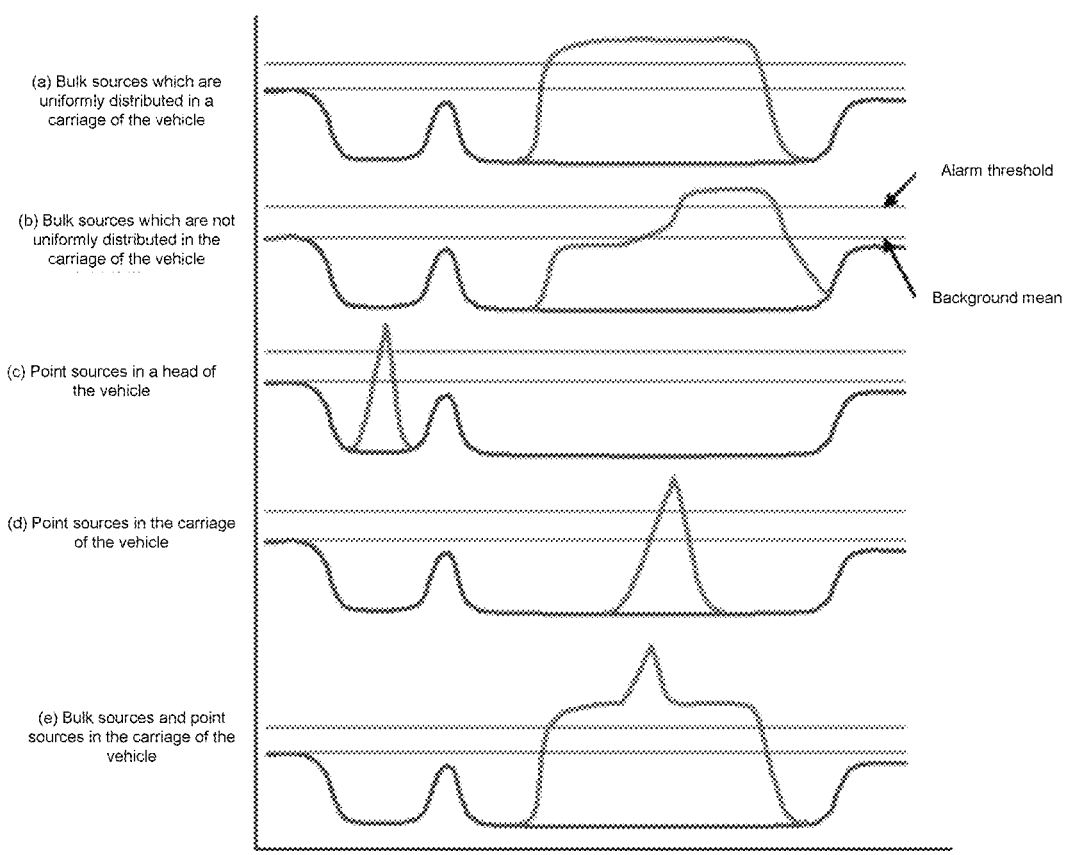
FIG. 4 is a diagram illustrating examples of shapes of count rate curves in many situations which trigger an alarm.
Figure 5:
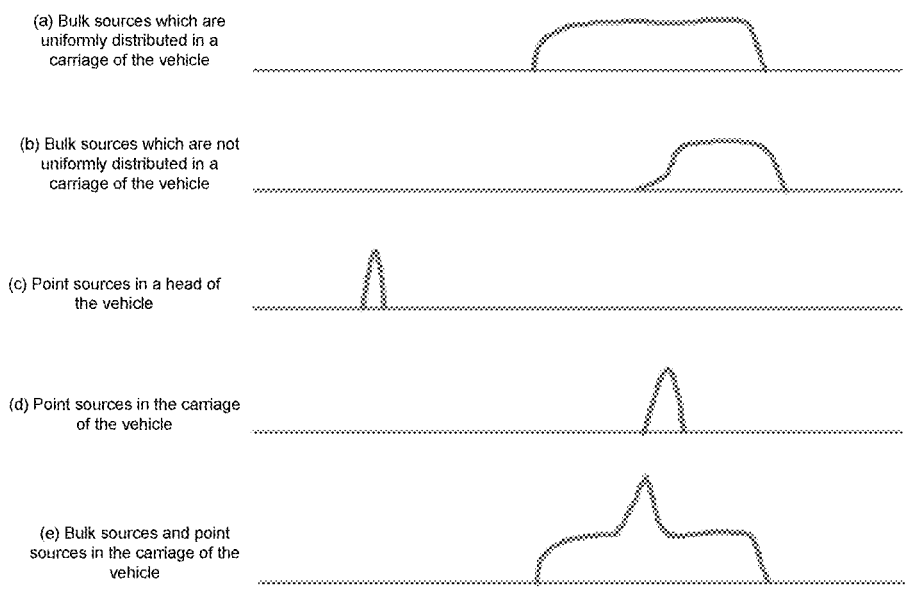
FIG. 5 is a diagram illustrating examples of shapes of the count rate curves corresponding to the various examples in FIG. 4 from which a background mean value has been removed.

In the process of the vehicle passing through the detection passage, if the count rate exceeds an alarm threshold at a certain time, an alarm is triggered. FIG. 4 is a diagram illustrating examples of shapes of count rate curves in many situations which trigger an alarm. FIG. 5 is a diagram illustrating examples of shapes of the count rate curves corresponding to the various examples in FIG. 4 from which a background mean value has been removed. In practice, the shape of the count rate curve is usually a combination of one or more of the several examples shown in FIGS. 4 and 5.

On this basis, a method for detecting radioactive sources according to an embodiment of the disclosed technology will be described below with reference to FIG. 6.

Figure 6:
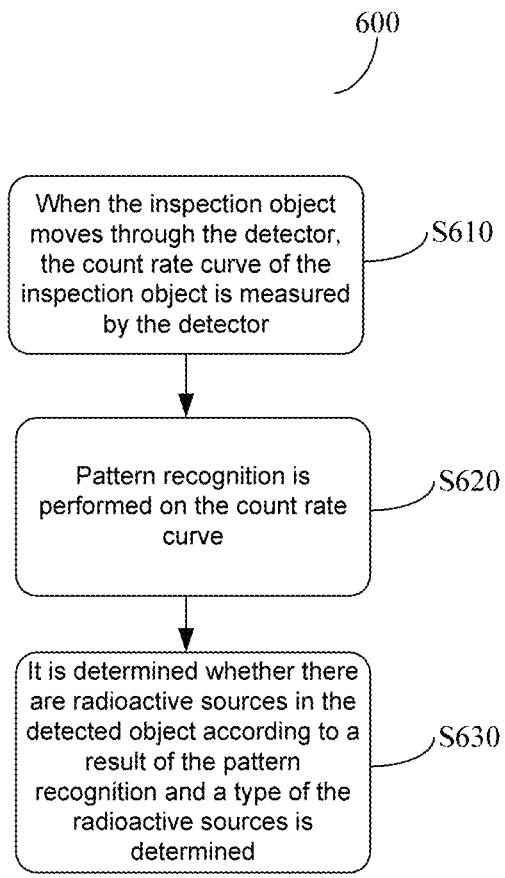
FIG. 6 is a flowchart of a method for detecting radioactive sources according to an embodiment of the disclosed technology.

FIG. 6 is a flowchart of a method 600 for detecting radioactive sources according to an embodiment of the disclosed technology. The method starts at step S610, where a count rate curve of an inspection object is measured by a detector while the inspection object moves through the detector. Then, in step S620, pattern recognition is performed on the count rate curve. Finally, in step S630, it is determined whether there are radioactive sources in the inspection object according to a result of the pattern recognition and a type of the radioactive sources is determined if there are radioactive sources in the inspection object.

In step S610, while the inspection object moves through the detector, the count rate curve of the inspection objected is measured by the detector.

"The count rate curve of the inspection object" refers to a curve formed by count rates detected on the detector during the inspection of the inspection object. In general, the detection starts from the inspection object being about to enter a detection range of the detector, until the inspection object is just out of the detection range of the detector. It will be understood by those skilled in the art that other time points may also be set as long as the detection can reflect the complete radioactive characteristics of the inspection object.

In step S620, pattern recognition is performed on the count rate curve.

It can be seen from FIGS. 2-4 that the count rate curves of the point radioactive sources and the bulk radioactive sources have a significant difference in shape. With the pattern recognition method, it may be determined whether a part of the obtained count rate curve has a shape corresponding to a typical spike-like curve of the point radioactive sources.

In one embodiment, performing the pattern recognition comprises performing pattern matching with a plurality of predetermined patterns. For example, the plurality of predetermined patterns may be shown in FIG. 4.

In an embodiment, the step of performing pattern recognition on the count rate curve comprises: calculating mathematical characteristics of the count rate curve; and performing pattern recognition according to a result of the calculation. For example, it may be determined whether there is a spike according to magnitude of decrease in counts on both sides of a maximum count rate value. Alternatively, it may be determined whether there is a spike by determining whether a statistical kurtosis exceeds a certain threshold through calculation. The kurtosis is a ratio of a fourth-order central moment of a random variable to a square of a variance of the random variable.

In one embodiment, the count rate curve may be a count rate curve from which a background mean value has been removed. A background level is shown in FIG. 4. In order to reduce the complexity of pattern recognition and improve the accuracy of pattern recognition, a part of the count rate curve which exceeds the background mean value may be cut out for analysis (as shown in FIG. 5).

In step S630, it is determined whether there are radioactive sources in the inspection object according to a result of the pattern recognition and a type of the radioactive sources is determined if there are radioactive sources in the inspection object.

In this step, it may be determined, based on the pattern recognition, which type of radioactive sources has a count rate curve consistent with the measured count rate, and thereby it is determined whether there are radioactive sources in the detected and a type of the radioactive sources is determined if there are radioactive sources in the inspection object.

In an embodiment, when the detection is performed, it may also be determined whether the inspection object stopped during the movement. Alternatively, it may be determined whether a minimum moving speed of the inspection object of the movement is higher than a preset threshold speed (and it may be determined whether the inspection object did stop when the threshold speed became 0). If the inspection object did stop during the movement, it may affect a shape of the measured count rate curve and cause damage to the solution according to the disclosed technology. Therefore, it is preferable that, in the technical solution according to the disclosed technology, if the inspection object ever stopped during the movement, the process proceeds back to the step of measuring a count rate curve of the inspection object for additional measurement.

In the scenario shown in FIG. 1, for example, it may be determined whether the vehicle stopped in the passage by at least the following: (1) calculating a time required for the vehicle to pass through the passage according to a speed of the vehicle (an average value of a speed at which the vehicle enters the passage and a speed at which the vehicle leaves the passage) and a length of the vehicle (which should be within a certain range), and determining that the vehicle stopped in the passage if a practical time for passing through the passage is greater than the required time (which is calculated by dividing the length of the vehicle by the average speed of the vehicle); (2) determining whether the vehicle stopped according to video monitoring in the passage; and (3) determining whether the vehicle stopped by installing a speedometer.

In one embodiment, the method further comprises a step of performing pattern recognition on the count rate curve only if a maximum count rate value in the count rate curve of the inspection object is higher than an alarm threshold. In this case, if the maximum count rate value in the detected count rate curve does not exceed the alarm threshold, it is considered that the inspection object does not contain sufficiently suspicious point radioactive sources and may not be taken into account.

Figure 7:
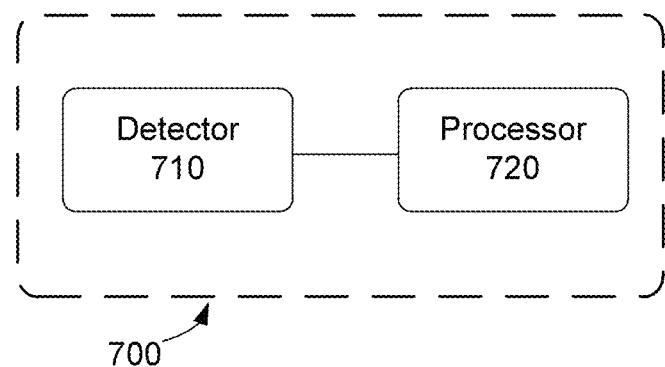
FIG. 7 is a structural block diagram of a device for detecting radioactive sources according to an embodiment of the disclosed technology.

FIG. 7 illustrates a structural block diagram of a device 700 for detecting radioactive sources according to an embodiment of the disclosed technology. The device 700 comprises a detector 710 and a processor 720. The detector 710 is configured inspect an inspection object passing therethrough. The processor 720 is connected to the detector 710 and is configured to perform operations of obtaining a count rate curve of the inspection object according to an inspection result from the detector; performing pattern recognition on the count rate curve; and determining whether there are radioactive sources in the inspection object according to a result of the pattern recognition and determining a type of the radioactive sources if there are radioactive sources in the inspection object.

The operations performed by the processor 720 of the device 700 for detecting radioactive sources correspond to the method 600 for detecting radioactive sources described above. The above specific description and explanation of the method 600 is equally applicable to the processor 720, and will not be described here again.

Figure 8:
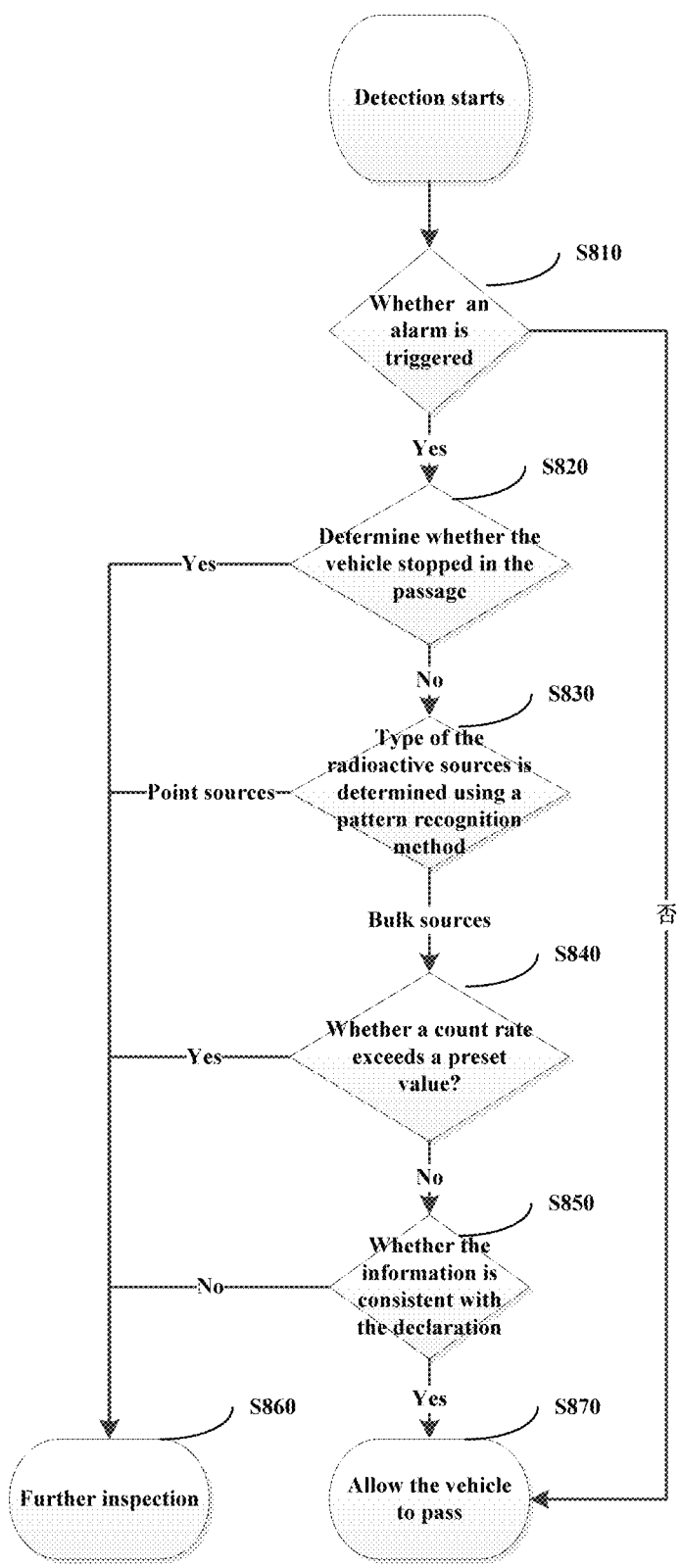
FIG. 8 illustrates an exemplary flow of practical radioactive material detection according to an embodiment of the disclosed technology.

FIG. 8 illustrates an exemplary flow of practical radioactive material detection in customs according to an embodiment of the disclosed technology.

In S810, after detection starts, it may firstly be determined whether an alarm is triggered. If there is no alarm, an inspection object may be allowed to pass; and if there is an alarm, the process proceeds to S820.

In S820, it is determined whether a vehicle stopped in a passage. If the vehicle stopped in the passage, the process proceeds to S860 for further inspection (or the vehicle is caused to pass through the detection passage again at a constant speed); and if the vehicle does not stop in the passage, the process proceeds to S830.

In S830, an appropriate pattern recognition method is used to analyze a shape of a count rate curve to determine a type of radioactive sources which trigger the alarm (point radioactive sources or bulk radioactive sources). If the radioactive sources are point radioactive sources, the process proceeds to S860 for further inspection; and if the radioactive sources are bulk radioactive sources, the process proceeds to S840.

In S840, for some users, even if the alarm is triggered by naturally occurring radioactive material, it is also necessary to distinguish the naturally occurring radioactive material in terms of intensity. In this case, it needs to preset a threshold. Once a count rate caused by the naturally occurring radioactive material exceeds this threshold, the process also proceeds to S860 for further inspection; and if the count rate caused by the naturally occurring radioactive material does not exceed this threshold, the process proceeds to S850.

In S850, for customs supervision, each vehicle has a corresponding declaration, and customs officers may make the decision whether to allow the vehicle to pass in combination with goods information in the declaration and type information of the radioactive sources.

In S860, for alarms triggered by point radioactive sources or bulk radioactive sources of which a count rate exceeds the preset threshold or bulk radioactive sources which are not consistent with content in the declaration, it needs to use a hand-held instrument for further inspection of the goods.

In S870, for alarms triggered by bulk radioactive sources which are consistent with the declaration and of which a count rate does not exceed the preset threshold, the vehicle may be allowed to pass.

One embodiment is described above in connection with FIG. 8. It will be apparent to those skilled in the art that one or more of the above steps are not essential and those skilled in the art can delete some of the steps or adjust an order of the steps according to different application scenarios.

While the disclosed technology has been illustrated in connection with the preferred embodiments of the disclosed technology, it will be understood by those skilled in the art that various changes, substitutions, and alterations can be made therein without departing from the spirit and scope of the disclosure. Accordingly, the disclosed technology should not be limited by the above-described embodiments, but rather should be defined by the appended claims and their equivalents.

The various features and processes described herein may be implemented independently of one another, or may be combined in various ways. All possible combinations and sub combinations are intended to fall within the scope of this disclosure. In addition, certain methods or process blocks may be omitted in some implementations. The methods and processes disclosed herein are also not limited to any particular sequence, and the blocks or states relating thereto can be performed in any other sequences that are appropriate. For example, described blocks or states may be performed in an order other than that specifically disclosed, or multiple blocks or states may be combined in a single block or state. The example blocks or states may be performed in serial, in parallel, or in some other manner as appropriate. Blocks or states may be added to or removed from the disclosed example embodiments as suitable. The example systems and components described herein may be configured differently than described. For example, elements may be added to, removed from, or rearranged compared to the disclosed example embodiments. Various embodiments can apply different techniques for fabricating different types of electronic devices.

While certain embodiments have been described, these embodiments have been presented by way of example only, and are not intended to limit the scope of the disclosure. Indeed, the novel devices, systems, apparatus, methods, and systems described herein may be embodied in a variety of other forms; furthermore, various omissions, substitutions and changes in the form of the methods and systems described herein may be made without departing from the spirit of the disclosure. For example, while blocks are presented in a given arrangement, alternative embodiments may perform similar functionalities with different components and/or circuit topologies, and some blocks may be deleted, moved, added, subdivided, combined, and/or modified. Each of these blocks may be implemented in a variety of different ways. Any suitable combination of the elements and acts of the various embodiments described above can be combined to provide further embodiments.

What is claimed is:

1. A method for detecting radioactive sources, comprising:
measuring, by a detector, a count rate curve of an inspection object while the inspection object moves through the detector, wherein the count rate curve is indicative of measured count rate varying with time;
determining whether a maximum count rate value in the count rate curve of the inspection object is higher than an alarm threshold;
performing pattern recognition on the count rate curve based on determining that the maximum count rate value in the count rate curve of the inspection object is higher than the alarm threshold; and
on the basis of the result of the pattern recognition, determining whether there are radioactive sources in the inspection object and whether the radioactive sources are bulk radioactive sources or point radioactive sources.

2. The method according to claim 1, further comprising:
determining whether movement of the inspection object satisfies a predetermined condition, and
if the movement of the inspection object does not satisfy the predetermined condition, causing the inspection object to move through the detector again and accordingly performing the measurement, pattern recognition and determination operations.

3. The method according to claim 2, wherein the predetermined condition is that the inspection object did not stop during the movement or a minimum moving speed of the movement was higher than a threshold speed.

4. The method according to claim 1, wherein the operation of performing pattern recognition on the count rate curve comprises:
calculating mathematical characteristics of the count rate curve; and
performing pattern recognition according to a result of the calculation.

5. The method according to claim 4, wherein the operation of performing the pattern recognition comprises performing pattern matching with a plurality of predetermined patterns.

6. The method according to claim 4, wherein the mathematical characteristics are a kurtosis of the curve or magnitude of decrease on both sides of a maximum value of the curve.

7. The method according to claim 1, wherein the count rate curve is a count rate curve from which a background mean value has been removed.

8. A device for detecting radioactive sources, comprising:
a detector configured to inspect an inspection object passing therethrough;

a processor connected to the detector and configured to perform operations of:

obtaining a count rate curve of the inspection object according to an inspection result from the detector, wherein the count rate curve is indicative of a measured count rate varying with time;

determining whether a maximum count rate value in the count rate curve of the inspection object is higher than an alarm threshold;

performing pattern recognition on the count rate curve based on determining that the maximum count rate value in the count rate curve of the inspection object is higher than the alarm threshold; and on the basis of the result of the pattern recognition, determining whether there are radioactive sources in the inspection object and whether the radioactive sources are bulk radioactive sources or point radioactive sources.

9. The device according to claim 8, wherein the processor is further configured to perform operations of:

determining whether movement of the inspection object satisfies a predetermined condition, and if the movement of the inspection object does not satisfy the predetermined condition, causing the inspection object to move through the detector again and accordingly performing the detection, pattern recognition and determination operations.

10. The device according to claim 9, wherein the predetermined condition is that the inspection object did not stop during the movement or a minimum moving speed of the movement was higher than a threshold speed.

11. The device according to claim 8, wherein the operation of performing pattern recognition on the count rate curve comprises:

calculating mathematical characteristics of the count rate curve; and performing pattern recognition according to a result of the calculation.

12. The device according to claim 11, wherein the operation of performing the pattern recognition comprises performing pattern matching with a plurality of predetermined patterns.

13. The device according to claim 11, wherein the mathematical characteristics are a kurtosis of the curve or magnitude of decrease on both sides of a maximum value of the curve.

14. The device according to claim 8, wherein the count rate curve is a count rate curve from which a background mean value has been removed.

* * * * *